United States Patent [19]

Takahashi et al.

[11] Patent Number: 5,494,821
[45] Date of Patent: Feb. 27, 1996

[54] PROCESS FOR SEPARATING OPTICALLY ACTIVE 1-HYDROXY-CYCLOPENTANE METHANOL DERIVATIVES USING LIPASE FROM CANDIDA OR PSEUDOMONAS

[75] Inventors: Eisaku Takahashi, Tokyo; Takashi Kimura, Kyoto; Satoru Kumazawa, Iwaki, all of Japan

[73] Assignee: Kureha Kagaku Kogyo K.K., Tokyo, Japan

[21] Appl. No.: 322,725

[22] Filed: Oct. 13, 1994

Related U.S. Application Data

[63] Continuation of Ser. No. 66,267, May 25, 1993, abandoned.

[30] Foreign Application Priority Data

May 29, 1992 [JP] Japan ................... 4-161809

[51] Int. Cl.$^6$ .................................................. C12P 41/00
[52] U.S. Cl. ..................... 435/280; 435/874; 435/921
[58] Field of Search ................................. 435/280, 135, 435/156, 874, 921

[56] References Cited

U.S. PATENT DOCUMENTS

| 4,607,013 | 8/1986 | Mitsuda et al. | 435/280 |
| 4,933,290 | 6/1990 | Cesti et al. | 435/280 |
| 5,142,061 | 8/1992 | Briner | 548/267.8 |
| 5,225,430 | 7/1993 | Minoguchi et al. | 514/383 |

FOREIGN PATENT DOCUMENTS

| 58-047495 | 9/1983 | Japan . |
| 3-53886 | 3/1991 | Japan . |

OTHER PUBLICATIONS

Jones JB, Tetrahedron 42:3351–3403 (1986).
Chemical Abstracts, vol. 107(23), 214288b, 1987.
Chemical Abstracts, vol. 107(13), 111964q, 1987.
Chemical Abstracts, vol. 103(25) 210372u, 1985.

*Primary Examiner*—Irene Marx
*Assistant Examiner*—S. Saucier
*Attorney, Agent, or Firm*—Lowe, Price, LeBlanc & Becker

[57] ABSTRACT

In the present invention, an optically active cis type 1,2-diol derivative of the following formula (I) is produced by reacting a cis type 1,2-diol derivative of the formula (I) with a carboxylic acid derivative of the formula (II) in the presence of a lipase:

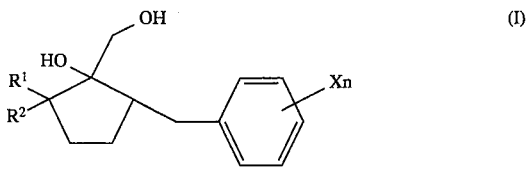

(I)

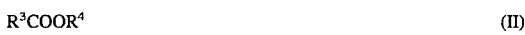

$R^3COOR^4$ (II)

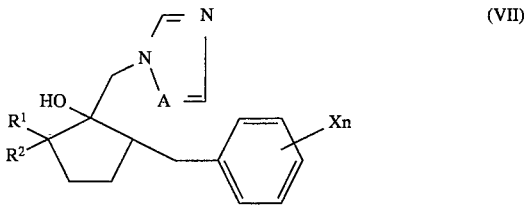

(VII)

wherein $R^1$ and $R^2$ independently represent hydrogen atom or an alkyl group, X represents a halogen atom, a nitro group, a cyano group, an alkyl group, a haloalkyl group, or a phenyl group, and n represents an integer of from 0 to 5; $R^3$ represents a $C_1$–$C_{10}$ alkyl group or an aryl group, and $R^4$ represents a hydrogen atom, a $C_1$–$C_5$ alkyl group, a $C_2$–$C_4$ alkenyl group, or $COR_3$.

The cis type means that the bond between the cyclopentane ring and the hydroxy group and the bond between the cyclopentane ring and the benzyl group reside in the same direction as that portrayed on the paper.

The optically active cis type 1,2-diol derivative is used as an intermediate for producing an optically active cis type azole derivative of the formula (VII).

5 Claims, No Drawings

PROCESS FOR SEPARATING OPTICALLY ACTIVE 1-HYDROXY-CYCLOPENTANE METHANOL DERIVATIVES USING LIPASE FROM CANDIDA OR PSEUDOMONAS

This application is a continuation of application Ser. No. 08/066,267 filed May 25, 1993, now abandoned.

BACKGROUND OF THE INVENTION

1. Field of the Invention

The present invention relates to a process for producing an intermediate for an optically active azole derivative, which is an effective ingredient for a fungicide.

2. Description of the Related Arts

It has been known that a cis type 1,2-diol derivative represented by the following formula (I) is an intermediate of a cis type azole derivative represented by the formula (VII) (see U.S. Pat. No. 5,142,061).

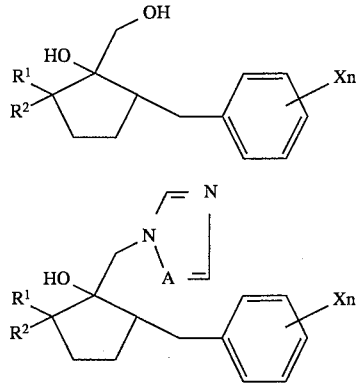

Even in the case of the azole derivatives of the formula (VII) depicted on similar plane formulae, the compound in which the bond between the cyclopentane ring and the hydroxyl group and the bond between the cyclopentane ring and the benzyl group reside in the same direction as portrayed on the paper (referred to as the "cis" type) has also been known to have higher activity than the compound in which these bonds reside in the reverse direction as portrayed on the paper (referred to as the "trans" type) (see U.S. Pat. No. 5,142,061).

Furthermore, later studies have proven that among the cis type azole derivatives of the formula (VII), one optical isomer from which the carbon on the cyclopentane ring having the hydroxyl group bonded thereto is more active than the other optical isomer in terms of the fungicidal activity and growth regulating activity.

An object of the present invention is, therefore, to provide a process for selectively producing a more highly active stereoisomer among the cis type azole derivatives represented by the formula (VII).

Here, the configuration of the compound is not distinguished by the direction of the bond as portrayed on this paper, but each bond is only depicted by a real line.

In the case where the cis type and the trans type are required to be distinguished, the "cis" type and "trans" type, respectively, are described.

SUMMARY OF THE INVENTION

The present inventors have continued serious research for the purpose of attaining the above object. As a result, it has been found that an optically active cis type 1,2-diol derivative represented by the formula (I) can be obtained when a cis type 1,2-diol derivative represented by the formula (I) is reacted with a carboxylic acid derivative represented by the formula (II) in the presence of a lipase.

The process for producing an optically active cis type 1,2-diol derivative represented by the following formula (I) according to the present invention comprises reacting a cis type 1,2-diol derivative represented by the formula (I) with a carboxylic acid derivative represented by the formula (II) in the presence of a lipase:

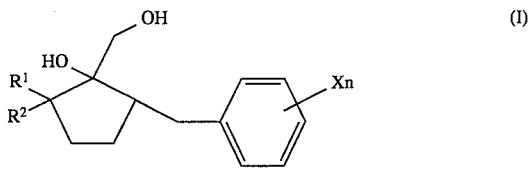

wherein $R^1$ and $R^2$ independently represent hydrogen atom or an alkyl group, X represents a halogen atom, a nitro group, a cyano group, an alkyl group, a haloalkyl group, or a phenyl group, and n represents an integer of from 0 to 5, when n is greater than 1, each X may be same or different;

$R^3$ represents a $C_1$–$C_{10}$ alkyl group or an aryl group, and $R^4$ represents a hydrogen atom, a $C_1$–$C_5$ alkyl group, a $C_2$–$C_4$ alkenyl group, or $COR_3$.

In the present invention, the cis type means that the bond between the cyclopentane ring and the hydroxy group and the bond between the cyclopentane ring and the benzyl group reside in the same direction as that portrayed on the paper.

The present inventors have also discovered that, when the optically active cis type 1,2-diol represented by the formula (I) obtained as described above is reacted with a sulfonyl halide represented by the formula (IV) to derive an optically active cis type sulfonic ester derivative of the formula (V), which is then substituted with an azole compound represented by the formula (VI) as shown in the following reaction formula, an optically active cis type azole derivative of the formula (VII) can be selectively produced.

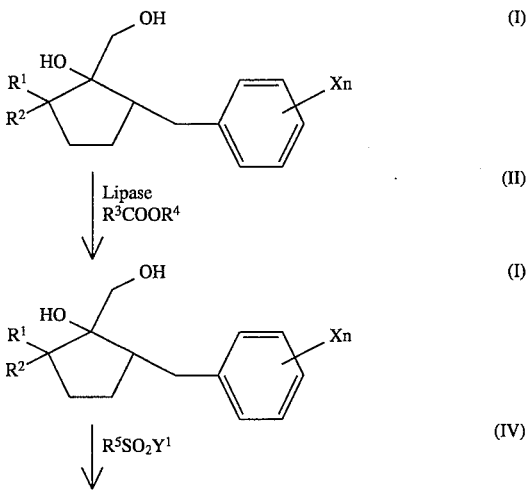

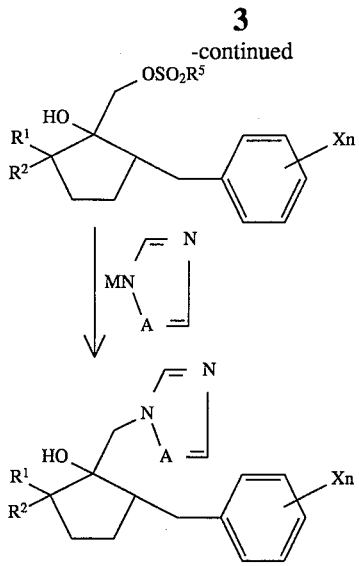

In the formula, the definitions of $R^1$–$R^5$, X, n, $Y^1$, A, and M will be the same as in the following description.

DETAILED DESCRIPTION OF THE INVENTION

The present invention will now be described in detail.

In the cis type 1,2-diol derivative of the following formula (I), which is used in the present invention $R^1$, $R^2$, X, and n have the following meanings.

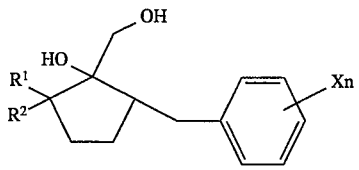

$R^1$ and $R^2$ independently represent a hydrogen atom or an alkyl group, preferably an $C_1$–$C_4$ alkyl group, X represents a halogen atom, preferably a fluorine atom, a chlorine atom, and/or a bromine atom, a nitro group, a cyano group, an alkyl group, preferably an $C_1$–$C_4$ alkyl group, a haloalkyl group, preferably an $C_1$–$C_4$ haloalkyl group, or a phenyl group, and n represents an integer of from 0 to 5, preferably an integer of from 0 to 2.

When n is greater than 1, each X may be same or different.

The carboxylic acid derivative which is used in the present invention is represented by the following formula (II).

wherein $R^3$ represents a $C_1$–$C_{10}$ alkyl group, preferably a $C_1$–$C_5$ alkyl group, or an aryl group, preferably a phenyl group which may have one or more substituents selected from the class consisting of halogen atoms, $C_1$–$C_3$ alkyl groups and $C_1$–$C_3$ alkoxy groups, and $R^4$ represents a hydrogen atom, a $C_1$–$C_5$ alkyl group, a $C_2$–$C_4$ alkenyl group, preferably a $C_2$–$C_3$ alkenyl group, or $COR_3$.

The amount of the aforementioned carboxylic acid derivative of the formula (II) to be used, expressed as the molar ratio relative to the aforementioned cis type 1,2-diol derivative of the formula (I), is preferably in the range of 1:0.5 to 1:30, and more preferably in the range of 1:0.9 to 1:15.

The lipase which is used in the present invention may be either one which is produced by a microorganism or one which originates from all animal or plant.

The term "lipase" used herein is a broad meaning of lipase, including esterase.

In the present invention, the lipase may be used in one of various forms such as a purified enzyme, a crude enzyme, an enzyme-containing substance, cultured liquor of a microorganism, a cultured substance, microorganisms cells, a cultured filtrate, or a treated product thereof.

Also, microorganisms may be used.

Specific examples of microorganisms which produce the lipase include, for instance, microorganisms belonging to the genus Enterobacter, the genus Arthrobacter, the genus Brevibacterium, the genus Pseudomonas, the genus Alcaligenes, the genus Micrococcus, the genus Chromobacterium, the genus Microbacterium, the genus Corynebacterium, the genus Bacillus, the genus Lactobacillus, the genus Trichoderma, the genus Candida, the genus Saccharomyces, the genus Rhodotorula, the genus Cryptococcus, the genus Torulopsis, the genus Pichia, the genus Penicillium, the genus Aspergillus, the genus Rhizopus, the genus Mucor, the genus Aureobasidium, the genus Actinomucor, the genus Nocardia, the genus Streptomyces, the genus Hansenula, and the genus Achromobacter.

The cultures of the above-enumerated microorganisms are generally carried out in a conventional manner; for example, an enzyme can be obtained by a liquid culturing.

For example, into a sterilized liquid medium, e.g., a malt extract/yeast extract medium (5 g of peptone, 10 g of glucose, and 8 g of a malt extract are dissolved in 1 liter of water, and the pH is adjusted to 6.5) for a fungi or an yeast, or a converted sugar-bouillon medium (10 g of glucose, 5 g of peptone, 5 g of meat extract,and 18 g of NaCl are dissolved in 1 liter of water, and the pH is adjusted to 7.2) for bacteria is inoculated a microorganism, and a shaking culture is carried out usually at 20° to 40° C. for 1 to 8 days. If necessary, a solid culture may be carried out.

Among the lipases originating from these microorganisms, several lipases are commercially available and, thus, readily available. Examples of commercially available lipases include a lipase originating from the genus Pseudomonas [Lipase P, (manufactured by Amano Seiyaku)], a lipase originating from the genus Aspergillus [Lipase A, (manufactured by Amano Seiyaku)], a lipase originating from the genus Mucor [Lipase M, (manufactured by Amano Seiyaku)], lipases originating from the genus Candida [Lipase AY (manufactured by Amano Seiyaku) and Lipase MY (manufactured by Meito Sangyo Co., Ltd.)], a lipase originating from the genus Alcaligenes [Lipase PL (manufactured by Meito Sangyo Co., Ltd.)], a lipase originating from the genus Achromobacter [manufactured by Shin-nippon Kagaku)], a lipase originating from the genus Chromobacterium [manufacture by Toyo Jozo Co., Ltd.], a lipase originating from the genus Rhizopus/Dermar [Talipase (manufactured by Tanabe Seiyaku Co., Ltd.)], an esterase originating from the genus Pseudomonas [Cholesterol/esterase (manufacture by Toyo Jozo Co., Ltd.)], and the like.

Examples of animal- or plant-originating lipases include steapsin, pancreatin, pig liver esterase, wheat malt esterase, etc.

Among them, a lipase originating from the genus Candida [Lipase AY (manufactured by Amano Seiyaku)] and a lipase originating from the genus Pseudomonas (manufactured by Sigma) are preferable in terms of their reactivity and other aspects.

These lipases may be purified or crude products, and they can be used individually or can be mixed as occasion may demand.

They can also be used as immobilized enzymes or cells which are immobilized onto a resin, etc.

In this case, they can be used in the form of a powder or granule. For example, an immobilized lipase in which one of the above lipases is carried on and immobilized onto a macromolecule such as polystyrene, polypropylene, starch, and gluten, or an inorganic material such as activated carbon, porous glass, celite, zeolite, kaolinite, bentonite, alumina, silica gel, hydroxyapatite, calcium phosphate, metal oxides, by a physical adsorption method, etc. is dried to be utilized.

After the reaction has been completed, the lipase recovered from the reaction liquor by filtration has a sufficient reactivity and a sufficient stereo-specificity and, thus, can be used repeatedly. Furthermore, such a lipase can be used for a continuous reaction.

In the present invention, aprotic organic solvents are preferably used as a reaction solvent. Examples include:

$C_4$–$C_7$ alkanes, such as n-hexane and isopentane;

$C_6$–$C_8$ cycloalkanes, such as cyclohexane and methylcyclohexane;

$C_1$–$C_2$ haloalkanes, such as chloroform and 1,2-dichloroethane;

aromatic hydrocarbons, such as benzene, toluene, and xylenes;

$C_2$–$C_4$ alkyl ethers, such as diethyl ether and diisopropyl ether; allcyclic ethers, such as tetrahydrofuran and tetrahydropyran; and others.

In the present invention, it is also possible not to use these aprotic organic solvents, but to use the carboxylic acid derivative of the formula (II) as the reaction solvent.

The reaction temperature is preferably from 15° C. to the boiling point of the solvent used, and preferably from 20° to 45° C.

The reaction period is varied depending upon various factors, such as the type of the carboxylic acid derivative of the formula (II) used and the amount thereof relative to the cis type 1,2-diol derivative of the formula (I), the type of the lipase used and the amount thereof relative to the cis type 1,2-diol derivative of the formula (I), the presence or absence of the solvent used and the type thereof, and the reaction temperature.

The amount of the lipase used can be determined depending upon the enzyme activity of the enzyme standard.

For example, it is preferably used in an amount of 0.01 to 10 times, more preferably 0.05 to 2 times, the weight of the cis type 1,2-diol derivative of the formula (I).

The reaction may be carried out with stirring, shaking, or left standing, but preferably with stirring or shaking.

The reaction operations of the present invention will now be specifically described.

In a reactor are weighed prescribed amounts of the substrate, a racemate of the cis type 1,2-diol derivative of the formula (I), of the carboxylic acid derivative of the formula (II), and of the lipase, and preferably an aprotic organic solvent such as toluene, benzene, or chloroform is added thereto in a prescribed amount.

The reaction is then carried out at a given temperature, preferably with stirring or shaking.

The progress of the reaction is monitored by determining the reaction amount of the cis type 1,2-diol derivative, with TLC or HPLC. When a prescribed amount has been reacted, the stirring or shaking is stopped, the reaction mixture is left standing, followed by filtration or centrifugal precipitation to remove the lipase.

The concentration of the filtrate in vacuo can give a reaction mixture containing an optically active cis type 1,2-diol derivative of the formula (I), which is substantially free of the antipode.

From the optically active cis type 1,2-diol derivative of the formula (I) obtained as described above, the optically active cis type azole derivative of the formula (VII) can be derived via a step of sulfoesterification and a step of substitution with an azole compound (VI).

Here, when the optically active cis type 1,2-diol derivative of the formula (I) is subjected to the subsequent steps, it can be used after being isolated or as it is in the reaction mixture.

(Sulfoesterification)

The optically active cis type sulfonic ester derivative of the formula (V) can be obtained, as shown in the following reaction formula, by subjecting the optically active cis type 1,2-diol derivative of the formula (I) to sulfoesterification in an organic solvent using benzenesulfonyl chloride, a substituted benzenesulfonyl chloride, or an alkanesulfonyl chloride, and a hydrochloric acid-capturing agent at a reaction temperature of 0° to 40° C. for a reaction period of 0.5 to 5 hours.

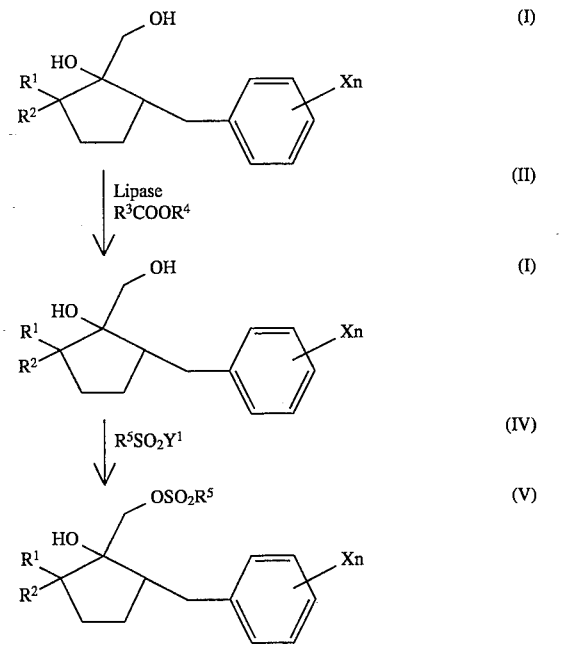

wherein $R^1$–$R^4$, X, and n are as defined above $R^5$ is a phenyl group, a substituted phenyl group, or an alkyl group, and $Y^1$ is a halogen atom.

A preferable example of the substituted benzenesulfonyl chloride is p-methylbenzenesulfonyl chloride, and a preferable example of the alkanesulfonyl chloride is methanesulfonyl chloride.

Examples of the hydrochloric acid-capturing agents which can be used include, but are not limited to, trimethylamine, triethylamine, N,N-dimethylaniline, N,N-diethylaniline, and the like.

Examples of the organic solvents which can be mentioned are aromatic hydrocarbons, such as benzene, toluene and xylene, aliphatic hydrocarbons, such as hexane, heptane and isooctane, halogenated alkanes, such as dichloromethane, chloroform and carbon tetrachloride, ethers, such as dioxane, THF, diethyl ether and diglym, and the like.

(Azolation Reaction)

The optically active cis type azole derivative of the formula (VII) can be obtained by subjecting the optically active cis type sulfonic ester derivative of the formula (V) to be substituted with an azole compound (VI), wherein A is a nitrogen atom or a CH group, M is a hydrogen atom or an alkali metal atom, in an organic solvent, optionally in the presence of a base, at a reaction temperature of 0° to 180° C. for a reaction period of 1 to 8 hours.

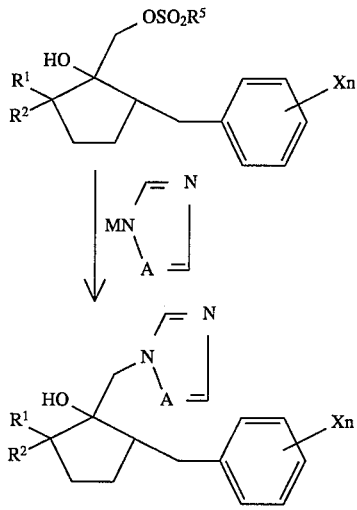

The amount of the base used in this reaction is preferably 2 to 100 times the mole of the optically active cis type sulfonic ester derivative of the formula (V).

Any inorganic or organic base can be used in this reaction, but preference is given to the use of potassium carbonate, potassium hydroxide, sodium carbonate, sodium hydroxide, and the like. Preferable examples of the organic solvents which can be used in this reaction step are aromatic hydrocarbons, such as benzene, toluene and xylene, aliphatic hydrocarbons, such as hexane, heptane and isooctane, halogenated alkanes, such as dichloromethane, chloroform and carbon tetrachloride, ethers, such as dioxane, THF, diethyl ether and diglym, aprotic polar solvents, such as acetonitrile, acetone, DMF, DMAC, DMSO, N-methylpyrrolidone and methyl isobutyl ketone, and the like.

According to the present invention, an optically active cis type 1,2-diol derivative, which can be used as an intermediate for an optically active cis type azole derivative of the formula (VII), can be obtained with good efficiency by reacting a cis type 1,2-diol derivative of the formula (I) with a carboxylic acid derivative of the formula (II) in the presence of a lipase.

EXAMPLES

The present invention will now be described by referring to the working examples, but the present invention should not be restricted thereto unless the examples deviate from the scope and the spirits of the present invention.

Referential Example 1

Preparation of Immobilized Enzyme

Into a 30 ml-volume vial bottle equipped with a spigot was put 0.3 g of Amano AY (manufactured by Amano Seiyaku), then 10 ml of 5 mM potassium phosphate buffer (pH 7.0) and 3.0 g of celite powder [Hiflowsuper Cell (manufactured by Kanto Kagaku)] were added thereto, and the content was stirred at 4° C. for 15 minutes. The resulting enzyme immobilized and adsorbed on the celite was spread over a Petri dish having a diameter of 90 mm, and dried in a vacuum desiccator overnight and then in the presence of phosphorus pentoxide for 2 days.

Referential Example 2

Preparation of (−)-cis-5-[4-chlorophenyl)methyl]-2,2-dimethyl-1-(1H-1,2,4-triazole-1-ylmethyl)cyclopentanol A) Synthesis of cis-5-[4-chlorophenyl)methyl]-2,2-dimethyl-1-(1H-1,2,4-triazole-1-ylmethyl)cyclopentanol In 30 ml of anhydrous dimethylformamide were dissolved 5 g of cis-7-[(4-chlorophenyl)methyl]-4,4-dimethyl-1-oxaspiro[2.4]heptane, and 2.2 g of 1H-1,2,4-triazole sodium salt were added in several portions with stirring. After the addition, the resulting mixture was stirred at 70° C. for 2 hours.

Subsequently, the reaction mixture was left cooling, then poured into ice-water, and extracted with ethyl acetate to obtain an organic phase. The organic phase was washed with saline, dried over anhydrous sodium sulphate, and the solvent was distilled off in vacuo.

The residue was purified with silica gel column chromatography, and further recrystallized from hexane/ethyl acetate to obtain 3.1 g of the title compound.

Yield: 49.2% Melting Point: 113°–114° C. $^1$H-NMR (CDCl$_3$, δ ppm) 0.60 (s, 3H), 1.00 (s, 3H), 1.07–1.90 (m, 3H), 2.33 (bs, 2H), 3.53 (s, 1H), 4.13 (s, 2H), 6,80–7.23 (m, 4H), 7.83 (s, 1H), 8.02 (s, 1H).

B) Separation of optically active (−) isomer

The azole derivative obtained in the above section A) was dissolved in methanol, fractionated with high performance liquid chromatography equipped with a column for separation of optically active isomer under the following conditions, and then recrystallized from a mixed solvent of ethyl acetate and hexanol to separate the (−)-cis-5-[4-chlorophenyl)methyl]-2,2-dimethyl-1-(1H-1,2,4-triazole-1-ylmethyl)cyclopentanol.

High performance liquid chromatography condition:
  Column: Chiralcell-OD, φ 10 mm×L 500 mm; produced by Daisel Chemical Co. Ltd.
  Pump: HITACHI 638-30; produced by Hitachi Ltd.
  Eluent: n-Hexane/isopropanol mixture=9/1
  Flow rate: 10 ml/min
  Detector: UV 268 nm
  Injection volume: 15 mg/150 μl (methanol)
  Retention time: 70 minutes.

The results of agricultural and horticultural activity tests of the optically active (−)-isomer obtained in Referential Example 2 are shown in Referential Examples 3 and 4.

This compound was also used as the authentic sample for identifying the compound obtained in the following Example 2.

Referential Example 3

Test for controlling effect against *Puccinia recondita* on wheat

Using the racemic or optically active isomer obtained in Referential Example 2 as an effective ingredient in each case, the ingredients described below each having the following weight ratio were pulverized and mixed to prepare a wettable powder, which was then diluted with water to be ready for use.

| | Parts by weight |
|---|---|
| Effective ingredient | 50 |
| Lignin sulfonate | 5 |
| Alkylsulfonate | 3 |
| Diatomaceous earth | 42 |

Onto the young seedlings of wheat of the second leaf stage (variety: NORIN No. 64, 16 seedlings per pot), which had been cultured while using unglazed pots of 10 cm in diameter, the wettable powder was diluted with water to give the suspension of the 3 ppm effective ingredient concentration and sprayed so as to be in a predetermined amount. After natural drying of the thus sprayed leaves, an aqueous suspension of uredospores of *Pucclnia recondita* collected from the attacked leaves of wheat was sprayed to inoculate on the thus dried leaves, and the treated seedlings were kept for 24 hours at a temperature of 20°–23° C. in a high humidity atmosphere.

Thereafter, the thus treated seedlings were left in a green house. After 7–10 days of the inoculation, the area rate of disease spots affected by *Puccinia recondita* was examined and the control value was calculated by the following formula.

$$\text{Control value} = \left(1 - \frac{\text{area rate of disease spots on treated pots}}{\text{area rate of disease spots on untreated pots}}\right) \times 100$$

| | Control value |
|---|---|
| Optically active (–) isomer | 99.3% |
| Racemate | 68.6% |

Referential Example 4

Test of plant growth controlling agent

Using the racemic or optically active isomer obtained in Referential Example 2 as an effective ingredient in each case, the ingredients described below each having the following weight ratios were uniformly mixed and dissolved to prepare an emulsifiable concentrate, which was then used with being diluted with water.

| | Parts by weight |
|---|---|
| Effective ingredient | 20 |
| Polyoxyethylene alkylaryl ether | 10 |
| Polyoxyethylene sorbitan monolaurate | 3 |
| Xylene | 67 |

Onto young seedlings of rice plant in the beginning of green leaf stage (variety: SASANISHIKI) grown in planters (30×60×3 cm), an emulsifiable concentrate diluted in 50 ppm with water was uniformly poured at a rate of 500 ml per planter. After cultured for 14 days in a green house, the plant length was measured and length controlling rate was calculated by the following formula.

$$\text{Length Controlling} = \left(1 - \frac{\text{Length in treated area}}{\text{Length in untreated area}}\right) \times 100$$

| | Length Controlling |
|---|---|
| Optically active (–) isomer | 34.6% |

$$\text{Length Controlling} = \left(1 - \frac{\text{Length in treated area}}{\text{Length in untreated area}}\right) \times 100$$

| | Length Controlling |
|---|---|
| Racemate | 12.4% |

EXAMPLE 1

Production of (+)-cis-5-[(4-chlorophenyl)methyl]-1-hydroxy-2,2-dimethylcyclopentane methanol (By optical resolution).

In a 10 ml-volume round bottom flask equipped with a spigot were put 100 mg of the celite absorbed and immobilized enzyme of Lipase AY (manufactured by Amano Seiyaku) prepared in Referential Example 1. Then, 50 mg of cis-5-[(4-chlorophenyl)methyl]-1-hydroxy-2,2-dimethylcyclopentane methanol (hereinafter referred to as "hydroxycyclopentane methanol" in Example 1), 168 mg of vinyl acetate, and 2 ml of toluene were added thereto, and the mixture was shaken at 37° C. for 5 hours.

After 5 hours, the area ratio of the remaining hydroxycyclopentane methanol to the formed acetate was 4: 6, which was determined by high performance liquid chromatography [column condition: 5C18-AR produced from Nakarai Tesk (φ 4.6 mm×150 mm), an aqueous 70% acetonitrile solution, 1.0 ml/min., detector: 268 nm].

Subsequently, the resultant mixture was taken out, the immobilized enzyme was removed by filtration under suction, and the solvent and other impurities were removed in vacuo. The hydroxycyclopentane methanol and α-acetate of cis-5-[(4-chlorophenyl)methyl]-1-hydroxy-2,2-dimethylcyclopentane methanol (hereinafter referred to as the "α-acetate") contained in the residue were separated by silica gel chromatography.

The results of several instrumental analyses are given for α-acetate.

IR (KBr,cm$^{-1}$): 3545, 2960, 1740. MS (EI method): [M+]=310. $^1$H-NMR (CDCl$_3$, δ ppm): 0.94 (3H, s), 1.08 (3H, s), 1.40 (2H, m), 1.70 (2H, m), 2.11 (3H, s), 2.12 (1H, s), 2.22 (1H, bs), 2.56 (1H, q, J=10.4, 13.5), 2.86 (1H, q, J=3.7, 13.5), 4.17 (2H, s), 7.10 (2H, d, J=8.5), 7.23 (2H, d, J=8.5).

The optical purity of the resulting hydroxycyclopentane methanol was determined according to the routine manner by high performance liquid chromatography equipped with an optical resolution column [column: Chiralcell-OD, φ 4.6 mm×250 mm; produced by Daisel Chemical Co. Ltd., eluent: n-hexane/isopropanol mixture=9/1].

Optical purity of (+) isomer: 95.0% ee.

EXAMPLE 2

Production of (–)-cis-5-[4-chlorophenyl)methyl]-2,2-dimethyl-1 -(1H-1,2,4-triazole-1-ylmethyl)cyclopentanol
(1) Production of (+)-cis-5-[(4-chlorophenyl)methyl]-1-hydroxy-2,2 -dimethylcyclopentane methanol (by optical resolution)

In a 50 ml-volume round bottom flask equipped with a spigot were put 2.00 g of the celite absorbed and immobilized enzyme of Lipase AY (manufactured by Amano Seiyaku), then 3.00 g of cis-5-[(4-chlorophenyl)methyl]-1-hydroxy-2,2 -dimethylcyclopentane methanol (hereinafter referred to as "hydroxycyclopentane methanol" in Example 2), 6.39 g of vinyl butyrate, 29 ml of toluene, and 1.5 ml of diglym were added thereto, and the mixture was shaken at 37° C. for 15 hours.

After 15 hours, the area ratio of the remaining hydroxycyclopentane methanol to the formed butyrate was 4:6, which was determined by high performance liquid chromatography [column conditions: 5C18-AR produced from Nakarai Tesk (φ 4.6 mm×150 mm), an aqueous 70% acetonitrile solution, 1.0 ml/min., detecter: 268 nm].

Subsequently, the resultant mixture was taken out, and the immobilized enzyme was removed by filtration under suction. The filtrate was evaporated under reduced pressure to remove the solvent and other impurities. The residue was a yellow oil and the yield was 3.42 g.

Optical purity of (+) isomer: 98.6. % ee.

(2) α-Methane sulfonation of (+)-cis-5-[(4-chlorophenyl)methyl]-1-hydroxy- 2,2-dimethylcyclopentane methanol Into a 10 ml-volume round bottom flask equipped with a spigot was put 1.00 g of the yellow oil obtained under (1), and 185 mg of methanesulfonyl chloride, 436 mg of triethylamine, 5 ml of toluene, and 0.2 ml of diglym were added thereto, followed by shaking at 40° C. for 3 hours. After the reaction had been ended, toluene and water were each added in an amount of 10 ml, and the toluene layer was separated by a fractionation operation. The water layer was further extracted with 15 ml of toluene. The resulting toluene layer was combined with the former toluene layer, and washed with water to be ready for the next reaction (3).

(3) Production of (−)-cis-5-[(4-chlorophenyl)methyl]-2,2-dimethyl-1-(1 H-1,2,4-triazole-1-ylmethyl]cyclopentanol A) The whole amount of the toluene solution obtained in the above section (2) was put in a 100 ml conical flask equipped with a spigot, then 15 ml of 25% (W/V) NaOH solution were added thereto, and the mixture was shaken at room temperature for 2 hours.

Subsequently, the toluene layer was separated, washed three times with each 5 ml of water, the toluene layer was dried over sodium sulfate, and the solvent was distilled off in vacuo to obtain 0.93 g of yellow oil.

B) Into a three-neck flask equipped with a spigot were put 133 mg of triazole and 267 mg of potassium carbonate, then 25 ml of DMF were added thereto, and the mixture was heated to 110° C. with stirring.

To the flask was added a solution in which 0.93 g of the yellow mentioned under section A) was dissolved in 2 ml of DMF in several portions over a period of 3 minutes. After the addition, the mixture was further stirred for 2 hours at 110° C. After the reaction had been ended, the reaction mixture was allowed to cool down to room temperature, poured into 70 ml of ice-water, and then extracted three times with each 70 ml of toluene.

The combined toluene layer was dried over sodium sulfate, and toluene was distilled in vacuo to obtain 0.95 g of yellow oil.

cis-5-[(4-Chlorophenyl)methyl]-2,2-dimethyl-1-(1H-1,2, 4-triazole-1-ylmethyl]cyclopentanol was separated from the resulting yellow oil by means of silica gel column chromatography (hexane/ethyl acetate=1/1).

Yield: 0.29 g. Yield from racemate of hydroxycyclopentane methanol: 34.7% Optical purity of (−) isomer: 99% ee.

What is claimed is:

1. A process for producing an optically active cis type 1,2-diol derivative of the formula (I), which comprises:

reacting a cis type 1,2-diol derivative of formula (I)

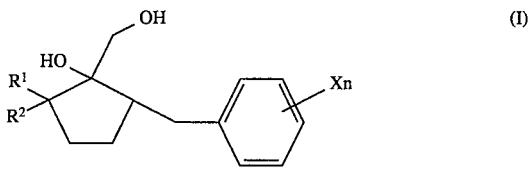

with a carboxylic acid of formula (II)

and a lipase from Candida or Pseudomonas which preferentially esterifies the antipods, wherein $R^1$ and $R^2$ independently are a hydrogen atom or an alkyl group, provided that $R^1$ is the same as $R^2$, X is a halogen atom, a nitro group, a cyano group, an alkyl group, a haloalkyl group or a phenyl group, n is an integer of from 0 to 5 and when n is greater than 1, each x may be the same or different, $R^3$ is a $C_1$–$C_{10}$ alkyl group or an aryl group, $R^4$ is a hydrogen atom, a $C_1$–$C_5$ alkyl group, a $C_2$–$C_4$ alkenyl group or $COR^3$, and recovering the optically active cis type 1,2-diol of formula (I) wherein cis type means that both the hydroxyl group and the benzyl group on the cyclopentane ring of formula (I) are bonded on the same side.

2. The process according to claim 1, further comprising the steps of:

reacting said optically active cis type 1,2-diol of formula (I) with a sulfonyl halide of formula (IV)

and a base to produce an optically active cis type sulfonic ester derivative of the formula (V)

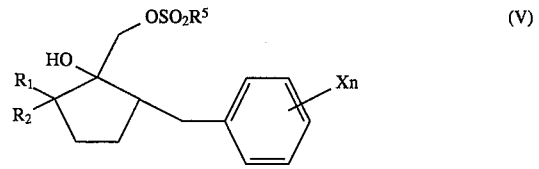

wherein $R^1$, $R^2$, X and n are defined above, $R^5$ is a phenyl group, a substituted phenyl group, or an alkyl group, and $Y^1$ is a halogen atom;

reacting said optically active cis type sulfonic ester with an azole compound of formula (VI), optionally in the presence of a base,

wherein A is a nitrogen atom or a CH group, M is a hydrogen atom or an alkali metal atom; and recovering an optically active cis type azole of formula (VII)

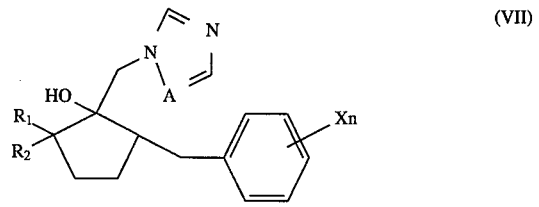

wherein $R^1$, $R^2$, X, n, and A are as defined above.

3. The process according to claim 1, further comprising the steps of:

reacting said optically active cis type 1,2-diol derivative of the formula (I) with a sulfonyl halide of the formula (IV) and a base $$R^5SO_2Y^1 \qquad (IV)$$

wherein $R^5$ is a phenyl group, a substituted phenyl group, or an alkyl group, and $Y^1$ is a halogen atom, to give an optically active cis type sulfonic ester derivative of the formula (V)

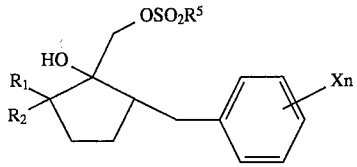

wherein $R^1$, $R^2$, X, n and $R^5$ are defined above and recovering the optically active cis type sulfonic ester of formula (V).

4. The process for producing an optically active cis type 1,2-diol derivatives claimed in claim 1, wherein the optically active cis type 1,2-diol derivative of formula (I) is (+)-cis-5-[4-chlorophenyl)methyl]-1-hydroxy-2,2-dimethylcyclopentane methanol.

5. The process for producing an optically active cis type 1,2-diol derivatives claimed in claim 1, wherein the lipase is an immobilized lipase which is carried on a carrier.

* * * * *